United States Patent [19]

Hammond

[11] Patent Number: 4,508,120
[45] Date of Patent: Apr. 2, 1985

[54] SUNTAN BOOTH

[76] Inventor: Steve A. Hammond, Walnut Park Mobile Estates #5, Spearfish, S. Dak. 57783

[21] Appl. No.: 418,376

[22] Filed: Sep. 15, 1982

[51] Int. Cl.³ .............................................. A61H 33/06
[52] U.S. Cl. .................................... 128/372; 128/373; 16/357
[58] Field of Search ................................ 128/371–373, 128/395, 399; 16/359, 360, 362, 363

[56] References Cited

U.S. PATENT DOCUMENTS

| | | | |
|---|---|---|---|
| 408,204 | 8/1889 | Babbitt | 128/372 X |
| 1,573,016 | 2/1926 | Pedroes | 128/373 X |
| 1,683,266 | 9/1928 | Shipman | 128/372 X |
| 1,733,756 | 10/1929 | Rittenhouse et al. | 128/372 |
| 2,098,316 | 11/1937 | Sittler | 128/373 |
| 2,167,489 | 7/1939 | Renga | 16/357 |
| 2,804,630 | 9/1957 | Gould | 16/360 X |
| 2,981,256 | 4/1961 | Besnah | 128/372 |
| 3,023,753 | 3/1962 | Wheless | 128/372 |
| 3,997,927 | 12/1976 | Culligan | 5/423 X |

FOREIGN PATENT DOCUMENTS 591175  6/1925  France .......................... 372/

Primary Examiner—Edward M. Coven
Attorney, Agent, or Firm—Harvey B. Jacobson

[57] ABSTRACT

A solar energy suntan booth including a heat collector plate mounted on a base for inclining the collector plate so that it is adapted for use as a surface for more effectively receiving the sun's radiation. The collector plate forms the top of an enclosed dead air space for receiving and retaining solar heat from the collector plate for transference back through the collector plate when it cools. The collector plate supports side extension members from the edges thereof and which are foldable from a collapsed position to an operating position serving to retain warmed air immediately above the collector plate thereby forming a layer of warm air within a space defined by the side extension members and collector plate. The collector plate and the side extension members are black for more effective heat absorption. The booth may be adjustably inclined and portable or of fixed inclined construction and the dead air space may have electric heater means to augment the heat collected in the dead air space. Piano hinges are mounted along two opposite sides of the collector plate and shackle hinges are mounted along the other two sides thereof, and the lower side extension is controlled by a handle member for adjusting its position for maximizing reception of solar energy and heat onto the collector plate.

5 Claims, 8 Drawing Figures

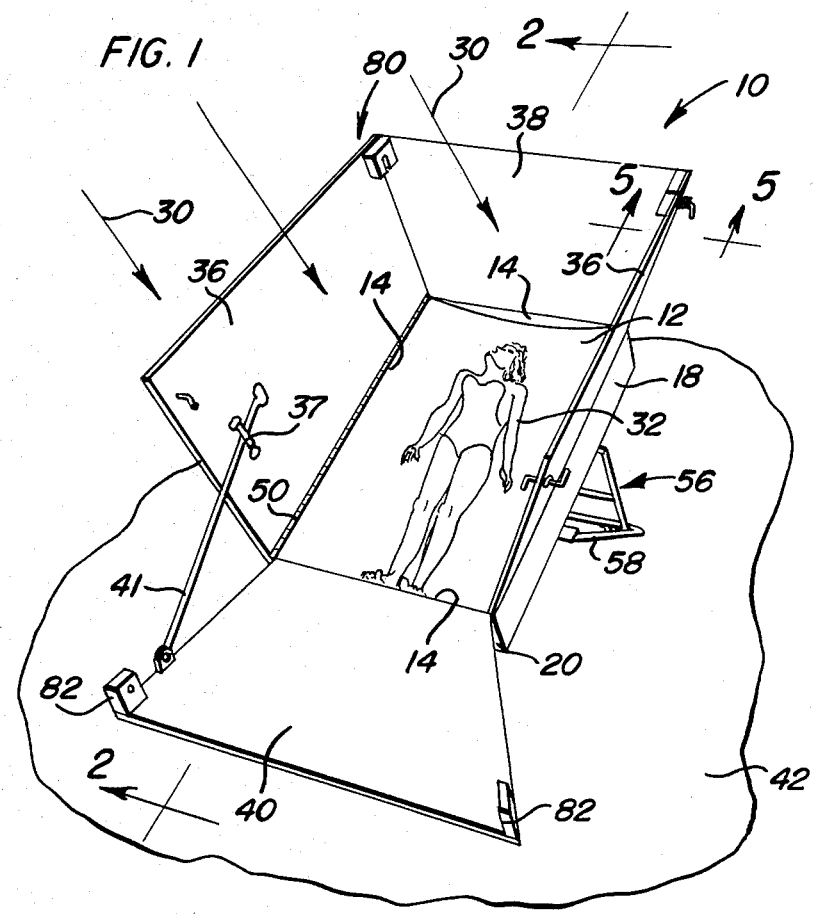

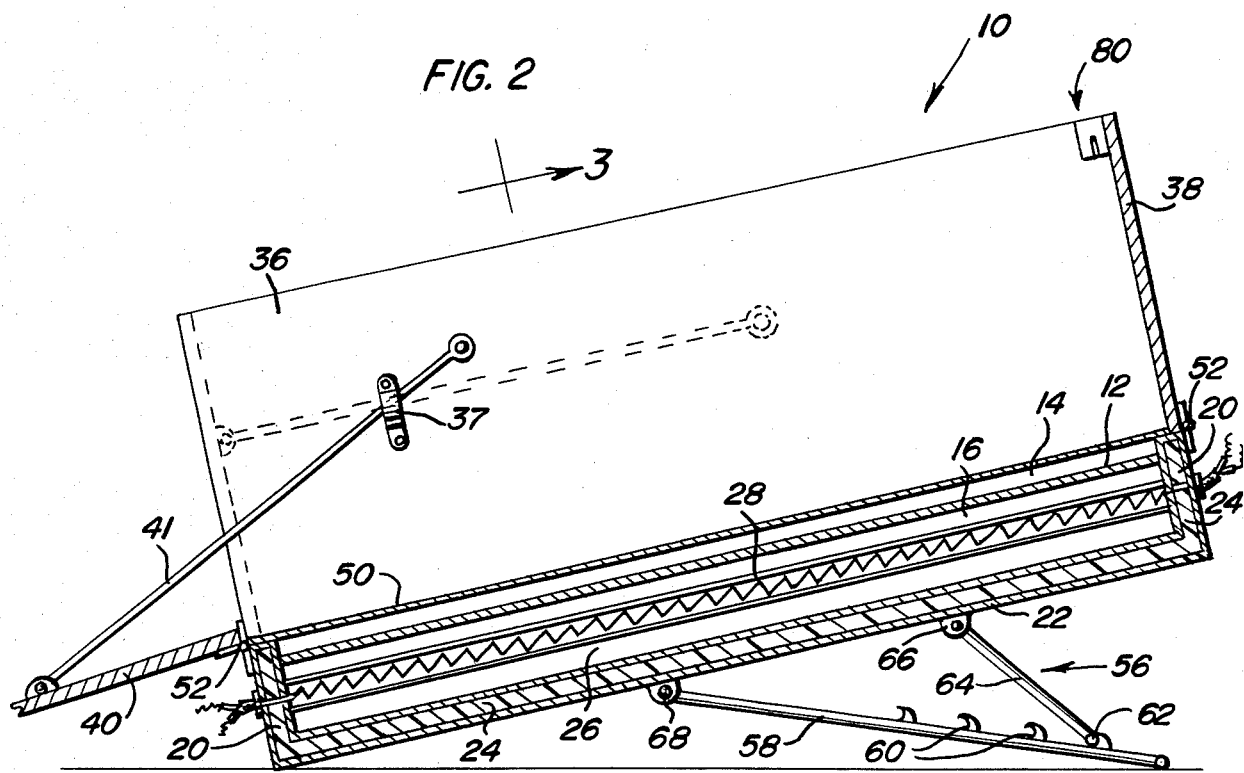
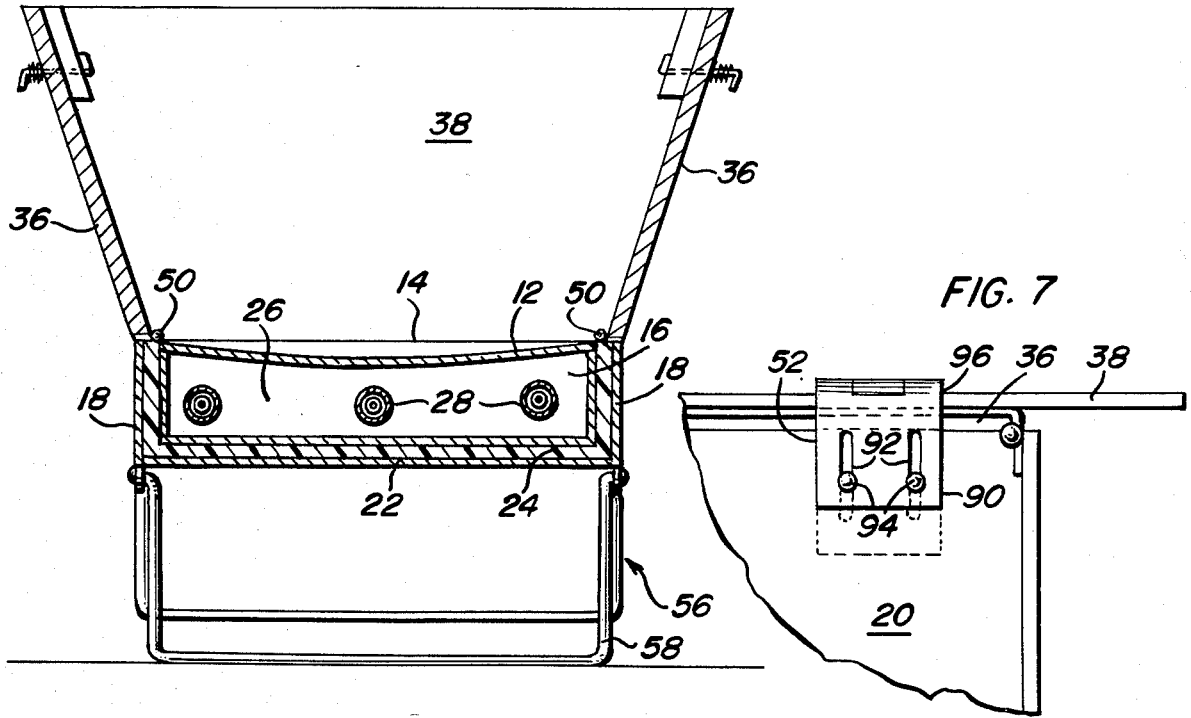

SUNTAN BOOTH

BACKGROUND OF THE INVENTION

1. Field of the Invention

The present invention relates to a solar energy suntan booth including a collector plate serving as a sun bathing area and forming part of a dead air space provided with layers of insulation, a heater coil and adapted to support the sun bather as well as maintain and return heat to the sun bather present on the collector plate, and having means supporting side extensions from each of the side edges of the collector plate forming the booth and being inclined for reception of solar energy. More particularly, the collector plate together with the supporting side extensions is constructed and arranged for conserving and retaining warmed air immediately above the collector plate and tending to form a thermal layer of warm air within a space defined by the side extensions and the collector plate. Hooks or fasteners are provided for separably securing corners of the side extensions in an assembled array, and disassembled when the side extensions are folded for storage. A slotted shackle hinge is provided where an outer folding side extension folds over an interior side extension.

2. Description of the Prior Art

The following U.S. patents relate to this invention: U.S. Pat. Nos. 407,434, S. D. Evans; 408,204, E. D. Babbitt; 1,669,484, C. D. Mowry; 1,733,756, W. Rittenhouse et al; 1,772,219, E. Kempton; 1,860,299, W. J. Strandwitz; 1,917,498, B. Collins; 1,964,463, W. L. Gittings; 2,981,256, G. A. Besnah; 3,023,753, L. M. Wheless; 3,688,775, E. F. Raymann; 3,997,927, R. L. Culligan; 4,140,128, J. Van Der Schaaf.

Each of the patents discloses a sun bath apparatus which merely allows an individual resting in the apparatus to receive a suntan. None of these patents discloses all of the specific details of the present invention in such a way as to bear upon the patentability of any claims of the invention.

SUMMARY OF THE INVENTION

An object and advantage of the present invention is to provide a solar energy suntan booth providing an inclined collector plate adapted to receive throughout its surface infrared and solar radiation in an outside environment, a dead air insulation space receiving heat from the collector plate and returning excess heat from the dead air space to the collector plate, the collector plate being configured generally to have rectangular edges, means supporting side extension members from each of the rectangular edges and adapted to fold from a collapsed position to an inclined position serving to isolate cold air currents and conserving warm air immediately above the collector plate and tending to form a thermal layer of warm air within a space defined by the side extensions and the collector plate. A basic principle of the solar heated booth is that it is constructed of a black color that absorbs the sun's infrared rays and warms the dead air space below the heat collector plate which in turn receives heat from the dead air space and in turn radiates warm air upwardly to warm the environment of the individual receiving the suntan and/or treatment.

Another object of the present invention is to provide for the booth to be portable, or to be stationary and that can be folded to a collapsed position for storage when not in use. While in the collapsed or folded position, the heat collector plate is protected from elements such as rain, snow, sun rays and other weathering conditions or forces.

Still another object of the present invention is to provide an arrangement of electrical heating coil with thermostat controlled heat and being installed within a dead air space to augment the solar energy suntan booth in utilizing the heat under adverse conditions of sun-received energy.

A further object of the invention is to provide a collector plate that is of a parabolic configuration assisting in focusing of sun energy onto the individual being suntanned or treated, and also within the purview of the invention is the object to provide a collector plate that has a double parabolic surface so that two people may lie in the booth together for the reception of solar energy or sun treatment. Also, an electrical shock prevention system such as a ground fault interruptor or the like is included in the electrical wiring for heater coils so that the system is completely safe from electrical shock.

An additional object of the present invention is to provide a booth having a movable end with a handle allowing for adjustment of its inclination when the height of the sun otherwise causes shadows. By movement of the lower side extension, its inclination can be adjusted to prevent shadows being cast on the patient or recipient of the sun's rays, or other space defined on the collector plate. The solar energy suntan booth can be made of one of several materials such as wood, fiberglass, sheetmetal, plastic, and the like.

A still further object of the present invention is to provide an arrangement of components for a solar suntan booth which maintains warm air around the person or persons obtaining the suntan while the top is open to allow the sun's ultraviolet rays to strike the person for suntanning, warm air from the metal collector plate rising and pushing upward toward cool air trying to fall into the warmed booth, and creating a thermal layer. This thermal layer acts as an invisible blanket keeping warm air in and cold air out while letting in the ultraviolet rays necessary for the tanning process while at the same time generating more warm air and maintaining continuously the thermal layer arrangement. No glass, glazing or cover of any kind covers the solar suntan booth since, to do so, would not allow ultraviolet rays to strike the person that is in the booth for receiving the suntan. Heat is kept in by the thermal layer of cool air over the warm air and the high inclined side extensions not only tend to create the thermal layer but also keep any cool breeze from chilling the person being suntanned.

Yet a still further object and advantage of the invention is to provide a back up heat system implemented for extra cool days especially when the sky is hazy or cirrus clouds do not allow sufficient amount of the sun's infrared rays to heat the solar suntan booth and impact upon the collector plate but do allow enough ultraviolet rays for tanning. The back-up heat is useful when on a sunny day an occasional cloud passes by and cools the booth and the person becomes uncomfortably cool. The back-up heat system is an arrangement of electrical coils thermostatically controlled in the dead air space and radiate heat up through the collector plate. In the use of the present invention, temperature readings inside the solar suntan booth are in a range of about 98° F. while the outside temperature is 42° F. The usefulness of the invention will keep one warm enough to obtain a suntan when the outside temperature is as low as 20° F. and it is useful for people who desire to obtain and maintain a tan virtually year round. The solar suntan booth can be installed or made portable for use on a patio or deck where the sun shines. A fold up or portable model where space is a premium and a stationary solar suntan booth is not practical. The portable model could be folded and stored until use was desirable.

Applications using the invention include winter resort areas such as ski resorts and lodges, hotels or motels at vacation oriented leisure installations or facilities as well as midday uses on a roof of a college dormitory, office building and other practical locations.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a front perspective view of a solar suntan booth according to the present invention.

FIG. 2 is a sectional view taken along lines 2—2 of FIG. 1.

FIG. 3 is a sectional view taken along lines 3—3 of FIG. 2.

FIG. 4 is a perspective view of a collapsed solar suntan booth according to the present invention.

FIG. 5 is a sectional view taken along lines 5—5 of FIG. 1.

FIG. 6 is a sectional view taken along lines 6—6 of FIG. 5.

FIG. 7 is an enlarged view of a slotted shackle hinge and taken along lines 7—7 of FIG. 4.

FIG. 8 is a perspective view of another embodiment of the present invention.

DESCRIPTION OF THE PREFERRED EMBODIMENTS

Referring now to the drawings, there is shown a solar energy suntan booth 10 having a collector plate 12 consisting of a parabolic surface in the transverse direction and a generally rectilinear surface in the longitudinal direction of the collector plate and being supported as well as made integral along its generally rectangular edges 14 with an insulated box or insulated enclosure 16 having opposite sidewalls 18 along the sides and the remaining sidewalls 20 at the head and the foot of the booth 10, and a bottom wall 22. The collector plate 12 forms a top wall of the insulated enclosure 16, and the sidewalls 18, 20, and the bottom wall 22, each contain a layer of insulation 24. The space bounded by the sidewalls 18, 20 and the bottom wall 22 taken together with the collector plate 12, defines a generally airtight enclosure or dead air space 26.

An auxiliary heating element or elements 28 is provided as a back up heat system for the booth 10 on extra cool days, especially when the sky is hazy or during the presence of cirrus clouds which do not allow a sufficient amount of the sun's infrared rays to heat the solar suntan booths 10 but do allow enough ultraviolet rays for tanning. Also, the back-up heat system including the heat elements 28 is useful when, on a sunny day, an occasional cloud passes by and cools the booth 10 and the person becomes uncomfortably cool. The heat elements 28 may be electrical coils thermostatically controlled by a resistor and manually operable switch assembly (not shown) and heat emanating from the heat elements 28 radiates into the dead air space 26 and upwardly to and through the collector plate 12. The collector plate may be a metal panel or the like, and the parabolic curvature of its surface in at least the one direction provides for focused radiation of heat energy therefrom onto the individual 32. The insulated enclosure 16 is generally well insulated throughout all sides except the side forming the top by the collector plate 12, and the collector plate 12 absorbs the heat of the sun's rays 30 and radiates heat energy onto the individual 32 and excess heat energy into the dead air space 26 in the insulated enclosure 16 and beneath the collector plate 12. The dead air space 26 in turn absorbs heat and the space 26 bounded by the insulated walls 18, 20, 22 provides that the heat is redirected to the collector plate 12 which in turn warms the individual 32 at a temperature sufficiently high enough to maintain the individual comfortable while suntanning in a swim suit even in the coldest of weather environmental condition.

The solar suntan booth 10 is provided along longitudinal edges 14 with relatively high sides 36, a head end side 38 adjacent the head of the individual 32 and a foot end side 40 which in total form the solar suntan booth 10. In cold belts, the solar suntan booth 10 is used where the ambient exterior temperature is, for example, 40°-42° F., and may be placed on a patio or deck 42 and which is usually adjacent a building or other permanent structure (not shown).

The sides 36 are supportably mounted and connected to sides 18 by piano hinges 50 that extend along the connecting edges between opposite side walls 18 and the high sides 36, but along the other two opposite sides 20, a set of shackle hinges 52 provide for the pivotal engagement between the sidewalls 20 and the sides 38-40. The interior surface and the exterior surface of the high sides or extensions 36, 38, 40, and the upper surface of the collector plate 12 are black which provides for heat and infrared energy reception and retention, and if desired, the entire assembly may have the surfaces black for heat reception and retention.

Along an intermediate bottom surface of the bottom wall 22 toward an end adjacent the head of the individual 32, there is a support frame or structure 56 including a base or rest frame 58 with notches 60 which are selective engageable adjustment projections for receiving an end bar 62 connected by a frame 64 to a pivot support 66 secured to the bottom wall 22. The frame rest 58 is also pivotally connected to the bottom wall 22 by pivot assembly 68. Use of the structure 56 and the frame rest 58 on the solar suntan booth 10 provides that the booth can be adjustably inclined as shown in FIGS. 1 and 2 through an angle, for example, between 15° and 25°.

A fixed support base made integral with the insulated enclosure 16 is shown in FIG. 8 for a stationary solar suntan booth. The configuration of the insulated enclosure 16 is not changed, but an additional portion is added to provide an integral stationary support base 70. Spaced available within the support base 70 exclusive of the area occupied by the insulated enclosure 16 may contain storage space for weather gear, wraps and the like while the individual 32 is using the solar suntan booth 72. For practical home uses, the solar suntan booth 10, 72 can be installed on the patio or deck 42 where the sunshine is available, and when not in use, the booth 10 can be folded up and stored.

At the outer marginal ends of the sides 38, 40 are provided locking assemblies 80 each including a block 82, see FIGS. 1 and 5, having an edge thereof securably affixed to a corresponding corner portion of walls 38, 40. A central portion of the block 82 has a generally eliptical or oval aperture 84 extending therethrough. In the adjoining portion of the sides 36, there is an eliptical or oval aperture 86 having an axis common to the axis of the aperture 84. The apertures 84, 86 being of the oval orientation are defined as having a short diameter and a long diameter, and there is provided a key or lock member 88 constructed such that it passes through the apertures 84, 86 when passed through or along the long dimensions of the aperture, but does not pass nor can it be withdrawn along the short diameter of the apertures 84, 86. The lock member 88 is a Z-shaped clip or lock member and its angulated portion is adapted to secure an acute portion adjacent the opening of the apertures 84, 86 along a short diameter thereof, and in this way the sides 36, 38, 40 are securely and firmly held in their open and fixed relation.

When the locking members 88 are withdrawn from the respective apertures 84, 86, the sides 36 are folded upon each other as shown in FIG. 4, and then the sides 38, 40 are folded over the collapsed sides 36, and this is accomplished by folding these sides 38, 40 by means of hinges 52. One of the leaves 90 of the hinges 52 contain slots 92, see FIG. 7, so that the leaves 90 can slide upwardly on stationary mounting bolts 94 until the leaves 90 are shown as in FIG. 7 with the mounting bolts 94 at the bottom of the slots 92. In this way, the leaves 90 are displaced upwardly so that a hinge pin 96 is projected above the combined folding or collapsing of sides 36 and the walls 40 is neatly and compactly folded over the collapsed sides 36 as illustrated in FIG. 4.

When the sides 36, 38, 40 are in their up and assembled position and are locked by locking assembly 80 at their four corners, these sides 36, 38, 40 cooperate to keep warm air around the individual 32, and while the top edges of the sides 36, 38, 40 are open allowing the sun rays to strike the individual 32 for suntanning, warm air from the collector plate 12 is accumulated between the sides 36, 38, 40 and above the collector plate 12 pushing generally upward and impacts with cool air trying to fall into the heated booth 10. This warm air creates a thermal body or layer within the booth 10 and this thermal layer performs or acts in a manner as an invisible blanket keeping the warm air in and cold air out of the booth, and ultraviolet rays 30 from the sun continue to proceed within the booth 10 and continuously provide the heat necessary for suntan, heating the collector plate and the insulated enclosure 16 and the tanning process of the skin of the individual 32 continues. Thus, there is no disadvantage of glass, glazing or covering of any kind provided to cover the booth 10 and the thermal body or layer described above maintain the individual 32 in the warm environment within the booth 10. This heated body or thermal layer is maintained by continued entry of sun's rays 30 entering the booth 10 and the thermal layer of cool air over the warm air in the booth continues. The sides 36, 38, 40 forming high sides not only create the thermal body or layer within the booth 10 but also keep out any of the cool breezes from chilling the individual 32 while suntanning. The individual 32 is able to keep warm enough to obtain a suntan even when the outside temperate is as low as 20° F. and therefore it is possible to obtain and maintain a tan virtually year round by use of the solar suntan booth 10 of the present invention. The foot end side 40 is provided with a rod-type handle 41 extending through a guide 37 on side 36 to open and close the side 40, which handle is disconnected when the booth is folded. Practical locations for use of the solar suntan booth 10 are at winter resort areas such as ski resorts and lodges. Hotels and motels could utilize the booth 10, particularly where it is a vacation oriented hotel or motel facility and leisure time would permit use of the solar suntan booths 10, 70. Also, the roof or sun decks of college dormitories, office buildings and the like would be a location adaptable for installation of such facilities for several solar suntan booths 10, 70 and which are capable of being used during short periods of time such as lunch hours when the impact of the sun's rays is generally the strongest.

It is possible within the purview of the present invention that a transparent covering may be of any of different kinds of glazing or some other transparent covering for allowing the passage of ultraviolet rays of the sun. The transparent covering may be bounded by a frame or edging for coupling over the upper and outer edges of the sides 36, 38, 40.

Essentially the invention provides, in summary, a solar booth that can be used by anyone that has arthritis or bursitis and the like. Warm infrared rays of the sun give soothing relief to people who suffer from any kind of inflammation of the joints or muscles, and including cases of bursitis due to divers having stayed down possibly too long and too deep and have a buildup of nitrogen in the joints which causes inflammation of the joints. The user of the solar booth receives absorption of heat by means of the invention and for the purposes as desired.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A collapsible solar energy suntan booth including a closed hollow enclosure of generally rectangular plan shape including opposite longitudinal side walls, opposite transverse end walls, a bottom wall extending and connected between the lower marginal portions of the side and end walls and a top wall defining solar energy absorbent collector plate extending and connected between the upper marginal portions of said side and end walls a pair of panel-shaped side extensions forming upward extensions of and hingedly supported from the upper marginal portions of said side walls for swinging between operative upwardly and outwardly inclined positions and collapsed positions closely overlying each other and said collector plate, a panel-shaped head end wall extension forming an upward extension of and hingedly supported from the upper marginal edge of one of said end walls enclosure for swinging between an operative upwardly projecting position extending between the adjacent ends of said side extensions when the latter are in their operative positions and a collapsed position closely overlying the adjacent ends of said side extensions when the latter are in the collapsed positions, and a panel-shaped foot and extension hingedly supported from the upper marginal portion of the other end wall of said enclosure for adjustable angular displacement between a lowered outwardly projecting position forming an endwise outward extension of said other end of said enclosure, an operative upwardly projecting position and a collapsed position closely overlying the adjacent ends of said side extensions when the latter are in their collapsed positions, releasable latch means connected between said side extensions and said head and foot end extensions operative to support said head and foot end extensions in the operative positions thereof when said side extensions are in their operative positions, said side extensions and foot and head end extensions, when in the operative position thereof, peripherally closing a dead air space therebetween above said enclosure, the surfaces of said extensions facing inwardly of said air space being of a dark solar energy absorbing color, said booth including base means underlying said enclosure and anchored relative thereto for supporting the latter in an inclined position from a generally horizontal surface and with said head end side uppermost, said foot end side, when in the lowered position thereof, defining a ramp leading upwardly into the interior of said booth, said foot end extension having one end of an elongated rod-type handle anchored relative thereto, one of said side extensions including guide means from which the other end of said handle is slidingly guided, said handle being operative by a person within said air space to selectively fully raise and lower said foot end extension, said latch means including a pair of coacting latch components mounted from each pair of adjacent side and end extension marginal edge portions and manually actuatable and releasable from both the inside and outside of said dead air space.

2. The booth of claim 1 wherein said panel-shaped side extensions are hingedly supported from said enclosure by piano hinges.

3. The booth of claim 1 wherein said head and foot end extensions are hingedly supported from the opposite end walls of said enclosure by shackle hinges mounted from opposite ends of said enclosure for limited vertical shifting relative thereto.

4. The booth of claim 1 wherein said enclosure includes internal auxiliary heating means.

5. The booth of claim 1 wherein said top wall is longitudinally straight and transversely upwardly concave.

* * * * *